United States Patent [19]

Kruse et al.

[11] Patent Number: 5,204,336
[45] Date of Patent: Apr. 20, 1993

[54] NAPHTHYL-,TETRAHYDRONAPHTHYL-, AND INDANYL-SUBSTITUTED G-EM-DIPHOSPHONATES AND PROCESS OF USE TO TREAT HYPERLIPIDEMIA

[75] Inventors: Lawrence I. Kruse, Malvern, Pa.; Virendra P. Shah, Welwyn, England

[73] Assignee: Symphar S.A., Geneva, Switzerland

[21] Appl. No.: 879,675

[22] Filed: May 6, 1992

Related U.S. Application Data

[63] Continuation-in-part of Ser. No. 703,237, May 20, 1991, abandoned, which is a continuation of Ser. No. 581,959, Sep. 13, 1990, abandoned.

[51] Int. Cl.$^5$ .................. A61K 31/66; C07F 9/40
[52] U.S. Cl. .......................... 514/107; 558/161
[58] Field of Search ................... 514/107; 558/161

*Primary Examiner*—Mary C. Lee
*Assistant Examiner*—Michael G. Ambrose
*Attorney, Agent, or Firm*—Wayne J. Dustman; Stephen Venetianer; Edward T. Lentz

[57] ABSTRACT

Substituted gem-diphosphonate compounds having use as cholesterol lowering agents are disclosed. A compound of the invention is tetraethyl-2-[3-t-butyl-4-hydroxynaphthyl]ethenylidene-1,1-diphosphonate.

43 Claims, No Drawings

NAPHTHYL-, TETRAHYDRONAPHTHYL-, AND INDANYL-SUBSTITUTED G-EM-DIPHOSPHONATES AND PROCESS OF USE TO TREAT HYPERLIPIDEMIA

This application is a continuation-in-part of application Ser. No. 703,237, filed May 20, 1991, now abandoned; which is a continuation of application Ser. No. 581,959, filed Sep. 13, 1990, now abandoned.

The present invention relates to novel naphthalene and tetrahydronaphthalene substituted gem-diphosphonate derivatives, processes for their preparation, pharmaceutical compositions containing them and their use in therapy, in particular in the treatment of hyperlipidaemia.

Substituted gem-diphosphonate derivatives are known in the art, for example, U.S. Pat. No. 4,696,920, discloses tetraethyl and tetrabutyl 2-(3,5-ditertiarybutyl-4-hydroxy)benzyl-1,3-propylidene diphosphonates and their use in the treatment of cardiovascular diseases; GB 2,043,072 discloses the synthesis of unsubstituted phenyl and phenoxy-alkylidene-1,1-diphosphonic acids and esters thereof and their application as antiatherosclerotic agents; and EP-339-237-A relates to a series of phenol substituted gem-diphosphonate derivatives which are disclosed as having antihyperlipidaemic activity.

The present invention provides, in a first aspect compounds of structure (I):

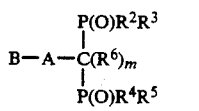
(I)

in which: B is 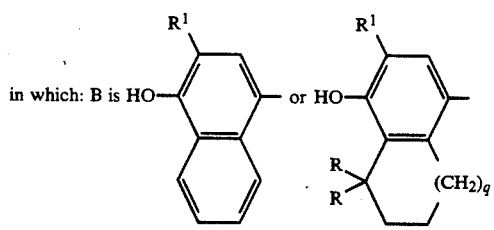

where
R is hydrogen or $C_{1-4}$alkyl and q is 0 or 1;
$R^1$ is hydrogen or $C_{1-8}$alkyl;
$R^2$, $R^3$, $R^4$ and $R^5$ are the same or different and are $OR^7$ in which $R^7$ is hydrogen or $C_{1-8}$alkyl; or $R^2$ and $R^3$ together and $R^4$ and $R^5$ together form a $C_{2-8}$alkylene dioxy ring;
$R^6$ is hydrogen or $C_{1-4}$alkyl;
m is 0 or 1, and
A is S, S(CH$_2$)$_n$, CH=CHCH$_2$, (CH$_2$)$_n$ or (CH=CH)$_p$(CH$_2$)$_t$CH= in which n is 1 to 7, p is 0 or 1 and t is 0 to 4, with the proviso that m is 0 only when A is (CH=CH)$_p$(CH$_2$)$_t$CH=.

Suitably each group R is the same and is hydrogen or $C_{1-4}$alkyl; preferably each group R is the same and is hydrogen.

Suitably q is 0 or 1; preferably q is 1.

Suitably, $R^1$ is hydrogen or $C_{1-8}$alkyl. Preferably, $R^1$ is $C_{1-4}$alkyl, in particular t-butyl.

Suitably, $R^2$, $R^3$, $R^4$ and $R^5$ are the same or different and are each $OR^7$, or $R^2$ and $R^3$ together and $R^4$ and $R^5$ together form a $C_{2-8}$alkylenedioxy ring. Preferably, $R^2$, $R^3$, $R^4$ and $R^5$ are the same and are each a group $OR^7$, in which $R^7$ is $C_{1-8}$alkyl, in particular, ethyl or i-propyl.

Suitably, $R^6$ is hydrogen or $C_{1-4}$alkyl; preferably $R^6$ is hydrogen.

Suitably m is 0 or 1, preferably m is 0.

Suitably A is S, S(CH$_2$)$_n$, CH=CHCH$_2$, (CH$_2$)$_n$ or (CH=CH)$_p$(CH$_2$)$_t$CH=; preferably A is (CH=CH)$_p$(CH$_2$)$_t$CH=; most preferably A is (CH=CH)$_p$(CH$_2$)$_t$CH= in which p and t are both zero.

The compounds of structure (I) can be prepared by processes analogous to those known in the art. In a further aspect of the present invention, there is therefore provided, a process for preparing compounds of structure (I) which comprises:

(a) for compounds of structure (I) in which A is S, S(CH$_2$)$_n$, CH=CHCH$_2$ or (CH$_2$)$_n$, reaction of a compound of structure (II):

(II)

in which B is as described for structure (I), $A^1$ is S, S(CH$_2$)$_n$, CH=CHCH$_2$ or (CH$_2$)$_n$, and Y is a leaving group with a diphosphonate of structure (III):

(III)

in which $R^2$ to $R^6$ are as described for structure (I);

(b) for compounds of structure (I) in which A is (CH=CH)$_p$(CH$_2$)$_t$CH=, reaction of an aldehyde of structure (IV):

(IV)

in which B, p and t are as described for structure (I) with a diphosphonate of structure (V)

(V)

in which $R^2$ to $R^5$ are as described for structure (I), in the presence of a base; or (c) for compounds of structure (I) in which A is (CH$_2$)$_n$, reduction of a compound of structure (VI):

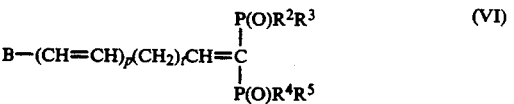
(VI)

in which, B, $R^2$ to $R^5$, p and t are as described for structure (I), and optionally thereafter,
hydrolysing the groups $R^2$ to $R^5$ in which $R^7$ is $C_{1-8}$alkyl to form compounds in which $R^7$ is hydrogen;
alkylating the groups $R^2$ to $R^5$ in which $R^7$ is hydrogen to form compounds in which $R^7$ is $C_{1-8}$alkyl.

Suitable leaving groups Y, will be apparent to those skilled in the art and include for example, halogen, in particular bromine or chlorine, or, for example, when $A^1$ is S, Y can be —SB, where B is as described for structure (I).

The reaction between a compound of structure (II) and a diphosphonate of structure (III) can be carried out in a suitable solvent at a suitable temperature up to the boiling point of the solvent used, in the presence of a base. Suitable solvents include, for example, hexane, heptane, benzene, toluene, tetrahydrofuran, dioxane, dimethoxyethane, methyl t-butyl ether or dimethylformamide. Suitable bases include, for example, sodium hydride, sodium alkoxide, n-butyl lithium or lithium diisopropylamide.

The reaction between a compound of structure (IV) and a diphosphonate of structure (V) can be carried out in a suitable solvent in the presence of a catalyst. Suitable solvents include for example tetrahydrofuran, dioxane or dimethoxyethane, in particular tetrahydrofuran. Suitable catalysts include, for example, titanium tetrachloride and a tertiary amine such as N-methyl morpholine or pyridine. Suitably, the reaction is conducted at a temperature of between 0° and ambient temperature, in particular at ambient temperature.

The reduction of compounds of structure (VI) can be carried out in a suitable solvent, in the presence of a reducing agent, at a temperature of between ambient and the reflux temperature of the solvent used, for example, the reduction can be carried out with a complex hydride reagent such as sodium borohydride or lithium borohydride in a polar solvent such as for example a $C_{1-4}$alkanol such as methanol or ethanol at a temperature of between ambient and the reflux temperature of the solvent used. Alternatively, the reduction can be carried out by catalytic hydrogenation using as the catalyst, a noble metal such as palladium or platinum adsorbed onto active charcoal. Suitable solvents for such hydrogenation include, for example, $C_{1-4}$alkanols such as methanol and ethanol, dimethyloxyethane, tetrahydrofuran and acetic acid. Preferably the reduction is carried out at room temperature, under a pressure of between 1 and 4 atmospheres.

The compounds of structure (I) have been found to be inhibitors of the enzyme acyl-CoA:cholesterol acyltransferase (ACAT), and as such are expected to be of use in therapy, in particular in the treatment of hyperlipidaemia and its related disease states, such as atherosclerosis. Furthermore, the compounds have been found to exhibit antioxidant properties which are also thought to be of benefit in the treatment of atherosclerosis. In addition, the compounds are expected to be of use as antiinflammatory, hypertensive, diuretic and positive inotropic agents.

In therapeutic use, the compounds of the present invention can be formulated into a standard pharmaceutical composition using methods well known to those skilled in the art of pharmacy. In a further aspect the present invention this provides pharmaceutical compositions comprising a compound of structure (I) in association with a pharmaceutically acceptable carrier.

The compounds of structure (I) which are active when given orally can be formulated as liquids, for example syrups, suspensions or emulsions, tablets, capsules and lozenges.

A liquid formulation will generally consist of a suspension or solution of the compound or pharmaceutically acceptable salt in a suitable liquid carrier(s) for example, ethanol, glycerine, non-aqueous solvent, for example polyethylene glycol, oils, or water with a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

A typical suppository formulation comprises a compound of formula (I) which is active when administered in this way, with a binding and/or lubricating agent such as polymeric glycols, gelatins or cocoa butter or other low melting vegetable or synthetic waxes or fats.

Preferably the composition is in unit dose form such as a tablet or capsule.

Each dosage unit for oral administration contains preferably from 1 to 250 mg (and for parenteral administration contains preferably from 0.1 to 25 mg) of a compound of the formula (I).

The present invention also provides a method of treatment of hyperlipidaemia which comprises administering to a mammal in need thereof an effective amount of a compound of the formula (I).

When used in therapy according to the present invention the daily dosage regimen for an adult patient may be, for example, an oral dose of between 1 mg and 500 mg, preferably between 1 mg and 250 mg, or an intravenous, subcutaneous, or intramuscular dose of between 0.1 mg and 100 mg, preferably between 0.1 mg and 25 mg, of the compound of the formula (I) the compound being administered 1 to 4 times per day. Suitably the compounds will be administered for a period of continuous therapy, for example for a week or more.

In addition, the compounds of the present invention can be co-administered with further active ingredients, such as other compounds known for the treatment of elevated lipid levels such as bile acid sequestrants and HMGCoA reductase inhibitors.

The following examples illustrate the invention. Temperatures are recorded in degrees centigrade.

EXAMPLE 1

Tetraethyl 2-3-t-butyl-4-hydroxynaphthyl]ethenylidene-1,1-diphosphonate (a) 1 3-t-Butyl-4-hydroxy-1-naphthaldehyde To a 0° solution of 2-t-butyl-1-naphthol (7.6 g, 0.038 mole) in 50 ml of dry dichloromethane was added anhydrous stannic chloride (19.77 g, 0.076 mole). The resulting reaction mixture was stirred at 0° during the dropwise addition of 1,1-dichloromethyl methyl ether (7.75 g, 0.068 mole). The mixture was stirred for 10 minutes at 0° then poured into ice/water. The resulting mixture was extracted with diethyl ether (3×200 ml). The ethereal extracts were washed with water until the aqueous washes had a neutral pH and then dried over magnesium sulphate. The solvent was removed in vacuo to give a solid residue which was triturated with a mixture of diethyl ether: n-pentane (1:4) to give 3.8 g (44% yield) of a crystalline solid, m.p. 195°–196°.

(b) Tetraethyl 2-[3-t-butyl-4-hydroxynaphthyl]ethenylidene-1,1-diphosphonate

Titanium tetrachloride (7.42 g, 0.039 mole) was added slowly with stirring to 50 ml of tetrahydrofuran (THF) (dried over 4A molecular sieves) at −10° to +5°. Then 2-t-butyl-4-hydroxy-1-naphthaldehyde (3.72 g, 0.0163 mole) and tetraethyl methylene diphosphonate (5.63 g, 0.0196 mole) were added to the mixture at 0°. N-Methyl morpholine (7.77 g, 0.0766 mole) was added dropwise to the reaction mixture such that the temperature remained below 5°. The reaction mixture was stirred for 2.25 hours at room temperature and was diluted with 100 ml of ice/water. The quenched reaction mixture was extracted with diethyl ether (3×200 ml) and the ethereal extracts were combined and washed with water until the aqueous washes had a neutral pH. The ether extract was washed with brine and dried over sodium sulphate then concentrated in vacuo to give a solid residue. The crude product was purified by chromatography on silica gel using ethyl acetate as eluant to give 7.4 g (85% yield) of yellow crystalline solid, m.p. 132°–134°.

Microanalysis: Found C, 57.81%; H, 7.26%; $C_{24}H_{36}O_7P$ requires C, 57.83%; H, 7.28%

EXAMPLE 2

Tetraisopropyl 2-3-t-butyl-4-hydroxynaphthyl]ethenylidene-1,1-diphosphonate

Dry tetrahydrofuran (60 ml) was cooled to −30° and titanium tetrachloride (9.08 g, 0.048 mole) was added slowly. To the resulting mixture was added 3-t-butyl-4-hydroxy-1-naphthaldehyde (4.57 g, 0.02 mole) followed by tetraisopropyl methylene diphosphonate (8.28 g, 0.024 mole). The resulting mixture was stirred as N-methyl morpholine (9.54 g, 0.094 mole) was added slowly while the temperature was maintained below 5°. After the addition was completed, the mixture was stirred for 4 hours at room temperature and 100 ml of ice/water was added. The quenched reaction mixture was extracted with diethyl ether (3×200 ml) and the combined ether extracts were washed with water until the aqueous washes were neutral pH. The ether solution was dried over anhydrous sodium sulphate and concentrated in vacuo to give a solid residue which was purified by column chromatography on silica using isopropyl acetate to give 9.2 g (80% yield) of a crystalline solid, m.p. 172°–173°. Microanalysis: Found C, 60.22%; H, 7.85%; $C_{28}H_{44}O_7P_2$ requires C, 60.15%; H, 8.02%.

EXAMPLE 3

Tetraispropyl 2-[3-tert-butyl-4-hydroxynaphthyl)ethylidene-1,1-diphosphonate

Tetraisopropyl 2-[3-tert-butyl-4-hydroxynaphthyl]-ethenylidene-1,1-diphosphonate (1.109 g, 0.002 mole) was dissolved in glacial acetic acid (50 ml) and the solution hydrogenated for 18 hours over 0.3 g of 10% palladium on carbon at 50 psi at room temperature. The catalyst was filtered and solvent was removed in vacuo. The residue was dissolved in diethyl ether and the solution was washed with aqueous sodium bicarbonate and water until the aqueous washes attained a neutral pH. The solution was washed with aqueous saturated sodium chloride and dried over anhydrous sodium sulphate. Solvent was removed in vacuo to give a solid residue which was recrystallised from dichloromethane n-pentane. The crystalline solid was filtered off and dried to give 0.95 g (85.3%) of the title compound, m.p. 146°–47°.

Microanalysis: Found C, 60.32%; H, 8.40%. $C_{28}H_{46}O_7P_2$ requires C, 60.42%; H, 8.33%.

EXAMPLE 4

Tetra-n-propyl 2-3-tert-butyl-4-hydroxy-1-naphthyl]ethenylidene-1,1-diphosphonate Titanium tetraphloride (8.34 g, 0.044 mole) was added dropwise to dry THF (60 ml) at −58°. The resulting mixture was treated wit 3-tert-butyl-4-hydroxynaphthaldehyde (4.56 g, 0.02 mole) and tetra-n-propyl methylene diphosphonate (7.57 g, 0.022 mole). N-Methyl morpholine (9.95 g, 0.098 mole) was added dropwise such that the temperature did not exceed +5°. The mixture was stirred for 135 minutes, poured into ice-water (30 ml) and extracted with diethylether (3×60 ml). The combined ethereal extracts were washed with saturated aqueous sodium bicarbonate, water, saturated aqueous sodium chloride, dried over anhydrous sodium sulphate and the solvent removed in vacuo. The residue was chromatographed on silica gel using ethyl acetate as eluant. The chromatographed material was triturated with a diethyl ether:n-pentane mixture (1:10) to give a yellow crystalline solid (9.3 g, 83.8%): m.p. 114°–115°. Microanalysis: Found: C, 60.85%; H, 8.05%. $C_{28}H_{44}O_7P_2$ requires: C, 60.64%; H, 7.99%.

EXAMPLE 5

Tetra-n-butyl 2-3-tert-butyl-4-hydroxy-naphthyl]ethenylidene-1,1-diphosphonate

Titanium tetrachloride (4.18 g, 0.022 mole) was added dropwise to dry THF (30 ml) at −58°. The resulting mixture was treated with 3-tert-butyl-4-hydroxynaphthaldehyde (2.28 g, 0.01 mole) and tetra-n-butyl methylene diphosphonate (4.40 g, 0.011 mole). N-methyl-morpholine (4.47 g, 0.044 mole) was added dropwise such that the temperature did not exceed +5°. The reaction mixture was stirred for 2 hours at room temperature, poured into ice-water (30 ml) and extracted with diethyl ether (3×60 ml). The combined ethereal extracts were washed with saturated aqueous sodium bicarbonate, saturated aqueous sodium chloride (to neutral pH) and dried over anhydrous sodium sulphate. Solvents were removed in vacuo and the residue chromatographed on silica gel using diethylether-dichloromethane (1:5) as eluant. The chromatographed material was triturated with n-pentane to give a crystalline solid (3.68 g, 63.2%): m.p. 86°–87°.

Microanalysis: Found: C, 62.77%; H, 8.55%. $C_{32}H_{52}O_7P_2$ requires: C, 62.93%; H, 8.58%

EXAMPLE 6

Tetraethyl 2-(3-tert-butyl-4-hydroxy-5,6,7,8-tetrahydronaphthyl)-ethenylidene-1,1-diphosphonate (a) 3-Tert-butyl-4-hydroxy-5,6,7,8-tetrahydronaphthaldehyde Stannic chloride (36.71 g, 0.141 mole) was added to a solution of 2-tert-butyl-5,6,7,8-tetrahydro-1-naphthol (16.0 g, 0.0783 mole) in dry dichloromethane (150 ml) at −10°. To the stirred solution was added 1,1-dichloromethyl methyl ether (13.45 g, 0.118 mole) dropwise at 0°. After 10 minutes, the reaction mixture was treated with ice-water and extracted with ethyl acetate (2×200 ml). The organic extract washed with aqueous saturated sodium chloride and dried over magnesium sulphate. The solvents were removed in vacuo and the solid residue was triturated with n-pentane:-diethyl ether (4:1) mixture to give a grey white crystalline solid which was filtered off and air-dried to yield 10.15 g (55.7%), m.p. 193°–94°.

(b) Tetraethyl 2-(3-tert-butyl-4-hydroxy-5,6,7,8-tetrahydronaphthyl)-ethenylidene-1,1-diphosphonate Dry tetrahydrofuran (150 ml) was stirred at −30° during the slow addition of titanium tetrachloride (9.08 g, 0.048 mole). The mixture was warmed at 0° and tetraethyl methylene diphosphonate (6.91 g, 0.024 mole) was added followed by 3-tert-butyl-4-hydroxy-5,6,7,8-tetrahydronaphthaldehyde (4.65 g, 0.02 mole). Then N-methyl morpholine (9.45 g, 0.091 mole) was added dropwise such that temperature did not exceed 5°. After 2.25 hours, the reaction mixture was mixed with silica gel (100 g) and washed with dichloromethane:ethanol mixture (10:1). The solvents were removed in vacuo to give a solid residue which was extracted with diethyl ether leaving a large amount of insoluble material. The diethyl ether was removed from the extract in vacuo and the residue was chromatographed on silica gel using ethyl acetate as an eluant to give a white solid residue which was triturated under n-pentane. The resulting crystalline solid was filtered off and washed with n-pentane and dried to yield 3.75 g (37.3%), m.p. 146°–47°.

Microanalysis: Found C, 57.08%; H, 7.88%; $C_{24}H_{40}O_7P_2$ requires C, 57.36%; H, 8.02%

EXAMPLE 7

Tetramethyl 2-(3-tert-butyl-4-hydroxy-5,6,7,8-tetrahydronaphthyl)-ethenylidene-1,1-diphosphonate Titanium tetrachloride (4.55 g, 0.024 mole) was added slowly to dry tetrahydrofuran (30 ml) which was stirred at −56°. The solution was warmed to 0° and 3-tert-butyl-4-hydroxy-5,6,7,8-tetrahydro-1-naphthaldehyde (2.33 q, 0.01 mole) was added, followed by tetramethyl methylene 1,1-diphosphonate (2.78 g, 0.012 mole). N-methyl-morpholine (4.8 g, 0.048 mole) was added dropwise at 0°–5°. The mixture was stirred for 5 hours and then poured into ice water and extracted with diethyl ether. The ethereal extracts were washed with water until the aqueous layer attained a neutral pH and the ethereal solution was washed with aqueous saturated sodium chloride solution and dried over anhydrous sodium sulphate. The solvent was removed in vacuo to give a residue which was chromatographed on silica gel using ethyl acetate as an eluant. The chromatographed material was triturated with n-pentane:dichloromethane (10:1) to give a crystalline solid which was filtered and dried to yield 0.72 g (16%), m.p. 149°–51°.

Microanalysis: Found C, 53.51; H, 6.98; $C_{20}H_{32}O_7P_2$ requires C, 53.61; H, 7.23.

EXAMPLE 8

Tetraisopropyl 2-[3-tert-butyl-4-hydroxy-5,6,7,8-tetrahydronaphthyl]-ethenylidene-1,1-diphosphonate Dry tetrahydrofuran (30.0 ml) was cooled to −56° while titanium tetrachloride (4.55 g, 0.024 mole) was added dropwise. The mixture was warmed to 0° and 3-tert-butyl-4-hydroxy-1-naphthaldehyde (2.33 g, 0.01 mole) and tetraisopropyl methylene-diphosphonate (4.13 g, 0.012 mole) were added. N-Methyl morpholine (4.80 g, 0.048 mole) was added dropwise at 0°–5°. After 3 hours the reaction mixture was quenched with 100 ml ice/water and extracted with diethyl ether (3×200 ml). The ethereal extracts were washed with water until the aqueous washes had a neutral pH and then with aqueous saturated sodium chloride. The solvent was removed in vacuo and the residue was chromatographed using isopropyl acetate as eluant to give 2.35 g of product which was washed with N-pentane and dried to yield 2.31 g (41.5%), m.p. 180°–82°.

Microanalysis: Found C, 60.12%; H, 8.49%; $C_{28}H_{48}O_7P_2$ requires C, 60.20%; H, 8.66%.

EXAMPLE 9

Tetraethyl 2-[3-tert-butyl-4-hydroxy-5,6,7,8-tetrahydronaphthyl]-ethylidene-1,1-diphosphonate Tetraethyl 2-[3-tert-butyl-4-hydroxy-5,6,7,8-tetrahydronaphthyl]ethenylidene-1,1-diphosphonate (1.005 g, 0.002 mole) was dissolved in glacial acetic acid (50.0 ml) and hydrogenated at 50 psi over 0.3 g 10% palladium on carbon at room temperature for 24 hours. The catalyst was filtered and the solvent was removed in vacuo. The residue was dissolved in diethyl ether (60 ml). The ethereal solution was washed with aqueous sodium bicarbonate solution, followed by water until the aqueous washes attained a neutral pH. The ether solution was washed with aqueous saturated sodium chloride and dried over anhydrous sodium sulphate. The solvent was removed in vacuo to give a residue which was triturated with diethyl ether/n-pentane. The solid was filtered and washed with n-pentane and dried to yield 0.81 g (80.3%) product: m.p. 84°–85°.

Microanalysis: Found C, 56.62%; H, 8.14%; $C_{24}H_{42}O_7P_2 \cdot 0.3H_2O$ requires C, 56.53%; H, 8.42%.

EXAMPLE 10

Tetraisopropyl 2-3-tert-butyl-4-hydroxy-5,6,7,8tetrahydronaphthyl]-ethylidene-1,1-diphosphonate A solution of tetraisopropyl 2-[3-tert-butyl-4-hydroxy-5,6,7,8-tetrahydronaphthyl]-ethenylidene-1,1-diphosphonate [1.117 g, 0.002 mole] in glacial acetic acid (50 ml) was hydrogenated over 10% palladium on charcoal (0.3 g) at 50 psi for 32 hours at room temperature. The catalyst was filtered, the solvent was removed in vacuo, and the residue was dissolved in diethyl ether (60.0 ml). The ethereal solution was washed with aqueous sodium bicarbonate solution, followed by water until the aqueous washes attained a neutral pH. The ethereal solution was washed with aqueous saturated sodium chloride solution, dried over anhydrous sodium sulphate, and concentrated in vacuo. The residue was chromatographed on silica gel using isopropyl acetate as an eluant. The chromatographed residue was dissolved in dichloromethane and excess n-hexane was added to give crystalline product which was collected and dried at 81°/0.1 mm to yield 0.62 g (55.3%), m.p. 119°–120°.

Microanalysis: Found C, 59.68%; H, 9.04%; $C_{28}H_{50}O_7P_2 0.25 H_2O$ requires C, 59.5%; H, 9.01%.

EXAMPLE 11

Tetra-n-propyl 2-[3-tert-butyl-4-hydroxy-5,6,7,8-tetrahydronaphthyl]ethenylidene-1,1-diphosphonate Titanium tetrachloride (4.18 g, 0.022 mole) was added dropwise to dry THF (30 ml) at −58°. The resulting mixture was treated with 3-tert-butyl-4-hydroxy-5,6,7,8-tetrahydronaphthaldehyde (2.35 g, 0.01 mole) and tetra-n-propyl methylene diphosphonate (3.79 g, 0.011 mole). N-methyl-morpholine (4.90 g, 0.0484 mole) was added dropwise such that the temperature did not exceed +5°. The mixture was stirred for 135 minutes at room temperature, treated with ice-water (30 ml) and extracted with diethyl ether (3×60 ml). The ethereal extracts were washed with water, aqueous sodium bicarbonate, aqueous saturated sodium chloride (to neutral pH) and dried over anhydrous sodium sulphate. The solvents were removed in vacuo and the residue chromatographed on silica gel using ethyl acetate as eluant. The chromatographed material was triturated with n-pentane to give a white crystalline solid which was dried to yield 3.19 g (57.1%), m.p. 129°–30°.

Microanalysis: Found: C, 60.38%; H, 8.65%; $C_{28}H_{48}O_7P_2$ requires: C, 60.20%; H, 8.66%.

EXAMPLE 12

Tetra-n-butyl 2-3-tert-butyl-4-hydroxy-5,6,7,8-tetrahydronaphthyl]ethenylidene-1,1-diphosphonate Titanium tetrachloride (4.18 g, 0.022 mole) was added to dry THF (30 ml) at −58°. The resulting mixture was treated with 3-tert-butyl-4-hydroxy-5,6,7,8-tetrahydronaphthaldehyde (2.35 g, 0.01 mole) and tetra-n-butyl methylene diphosphonate (4.40 g, 0.011 mole). N-methyl morpholine (4.47 g, 0.044 mole) was added dropwise such that the temperature did not exceed +5°. The mixture was stirred for 2 hours at room temperature, poured into ice-water (50 ml) and extracted with diethyl ether (3×60 ml). The ethereal extracts were washed with water saturated aqueous sodium chloride (to neutral pH) and dried over anhydrous sodium sulphate. The solvents were removed in vacuo and the residue chromatographed on silica gel using dichloromethane-ethyl acetate (10:1) as eluant. The chromatographed material was triturated with n-pentane to give a crystalline solid which was dried for 2 hours to yield 5.05 g (82.1%) m.p. 103°–104°.

Microanalysis: Found: C, 62.52%; H, 9.20%; $C_{32}H_{56}O_7P_2$ requires: C, 62.52%; H, 9.18%.

EXAMPLE 13

Tetra-n-propyl 2-[4-hydroxy-3-methyl-1-naphthyl]ethenylidene-1,1-diphosphonate 2-Methyl-1-naphthol (7.0 g, 44.2 mmole) and 1,1-dichloromethyl-methyl ether (7.12 g, 61.9 mmol) were dissolved in dry dichloromethane (150 ml). To the stirred solution stannic chloride (20.72 g, 79.6 mmole) was added dropwise at −58°, the mixture stirred for 45 minutes, and warmed to +10°. It was poured onto ice-water (200 ml) and extracted with ethyl acetate (2×100 ml). The extract was washed with aqueous saturated sodium chloride solution, dried and evaporated. The residue solidified on trituration under diethyl ether:n-pentane (1:10) mixture, was filtered off and chromatographed on silica gel using dichloromethane as eluant to give 4-hydroxy-3-methyl-1-napthaldehyde as a buff coloured crystalline solid, (5.3 g, 64.4%), m.p. 160°–61°.

To a stirred mixture of titanium tetrachloride (2.10 g, 11 mmole) in dry tetrahydrofuran (30 ml) at −58°, 4-hydroxy-3-methyl-1-naphthaldehyde (0.940 g, 5 mmole) and tetra-n-propyl methylene diphosphonate (1.89 g, 5.5 mmole) were added, and the reaction mixture warmed to −10°. N-methyl morpholine (2.45 g, 24.2 mmole) was added dropwise such that the reaction temperature did not exceed 10°. The reaction mixture was stirred for 3.25 hours at room temperature and then was poured onto ice-water (100 ml). It was extracted with dietyl ether (3×100 ml). The etherial extract was washed with water and aqueous saturated sodium chloride, dried and evaporated and the residue chromatographed on silica gel using ethyl acetate as elutant to give tetra-n-propyl 2-(3-methyl-1-naphthyl)ethenylidene-1,1-diphosphonate as a yellow oil (2.3 g, 90%).

Found: C, 57.65%, H, 7.20%, $C_{25}H_{38}O_7P_2 0.4H_2O$ requires: C, 57.77%, H, 7.52%

EXAMPLE 14

Tetra-n-butyl 2-4-hydroxy-1-naphthyl]ethenylidene-1,1-diphosphonate

Titanium tetrachloride (4.18 g, 22 mmole) was added slowly to dry tetrahydrofuran (60 ml) which was stirred at −58°. To the resulting yellow suspension 4-hydroxy1-naphthaldehyde (1.73 g, 10 mmole) and tetra-n-butyl methylene diphosphonate (4.4 g, 11 mmole) were added. The mixture was warmed to −10° and N-methyl morpholine (4.90 g, 48.4 mmole) in dry tetrahydrofuran (10 ml) was added dropwise such that the reaction temperature did not exceed +5°. The reaction mixture was stirred for 3.25 hours, poured onto ice-water (50 ml) and extracted with diethyl ether (4×100 ml). The ethereal extract was washed with water, aqueous sodium bicarbonate and aqueous saturated sodium chloride, dried and evaporated and chromatographed on silica gel using dichloromethane: ethyl acetate (20:1). The product solidified when cooled at −10° to give tetra-n-butyl 2-[4-hydroxy-1-napthyl]-ethenylidene-1,1-diphosphonate as a solid (2.6 g, 46.7%) m.p. 45°–46°.

Found: C, 60.85%, H, 8.04%. $C_{28}H_{44}O_7P_2$ requires: C, 60.64%; H, 8.00%.

EXAMPLE 15

Tetra-n-propyl 2-[4-hydroxy-1-napthyl ethenylidene-1,1-diphosphonate

Titanium tetrachloride (4.18 g, 2 mmole) was added to dry tetrahydrofuran (60 ml) which was stirred at −58°. 4-Hydroxy-1-napthaldehyde (1.73 g, 10 mmole) and tetran-propyl methylene diphosphonate (3.79 g, 11 mmole) were added to the reaction mixture which was warmed to −10°. N-methyl-morpholine (4.9 g, 48.4 mmole) was added dropwise such that the temperature did not exceed +5°. After 3.25 hours, the reaction mixture was poured onto ice-water (100 ml) and extracted with diethyl ether (4×100 ml). The ethereal extract was washed with water and aqueous saturated sodium chloride, dried and evaporated. The residue was chromatographed to give the title compound as a solid (3.35 g, 67.2%), m.p. 89°–90°.

Found C, 57.92%; H, 7.27%; $C_{24}H_{36}O_7P_2$
requires: C, 57.82%; H, 7.28%.

EXAMPLE 16

Tetra-isopropyl 2-4-hydroxy-1-naphthyl]ethenylidene-1,1-diphosphonate

Titanium tetrachloride (4.19 g, 22 mmole) was added to dry tetrahydrofuran (60 ml) which was stirred at −58°. 4-Hydroxy-1-napthaldehyde (1.73 g, 10 mmole) and tetra-isopropyl methylene diphosphonate (3.79, 11 mmole) were added to the reaction mixture which was warmed to −10°. N-methyl morpholine (4.9 g, 48.4 mmole) was added dropwise so that the temperature of the reaction mixture did not exceed +5°. The reaction mixture was stirred for 3.25 hours at room temperature. Then it was poured into ice-water (100 ml) and extracted with diethyl ether (4×100 ml). The ethereal extract was washed with water and aqueous saturated sodium chloride, dried and evaporated. The residue was chromatographed on silica gel using ethyl acetate as eluant, to give tetra-isopropyl 2-[4-hydroxy-1-naphthyl-]ethenylidene-1,1-diphosphonate as an oil (2.38 g, 48%).

Found: C, 57.72%; H, 7.24%, $C_{24}H_{36}O_7P_2$
requires C, 57.82%; H, 7.28%.

EXAMPLE 17

Tetraethyl 2-[4-hydroxy-1-naphthyl]-ethenylidene-1,1-diphosphonate

Titanium tetrachloride (4.19 g, 22 mmole) was added to dry tetrahydrofuran (60.0 ml) which was stirred at −58°. 4-Hydroxy-1-naphthaldehyde (1.73 g, 10 mmole) and tetraethyl methylene diphosphonate (3.17 g, 11 mmole) were added. The reaction mixture was warmed to −10°. N-Methyl morpholine (4.89 g, 48.4 mmole) was added dropwise so that the temperature did not exceed +5°. The reaction mixture was stirred for 3.25 hours at room temperature. It was poured into ice-water (100 ml) and extracted with diethyl ether (4×100 ml). The ethereal extract was washed with water and aqueous saturated sodium chloride, dried and evaporated. The residue was chromatographed on silica gel using ethyl acetate as an eluant to give the title compound as a solid (3.75 g, 84.7%), m.p. 139°–40°.

Found: C, 54.29%; H, 6.39%, $C_{20}H_{28}O_7P_2$
requires C, 54.30%, H, 6.38%.

EXAMPLE 18

Tetra-n-butyl 2-[4-hydroxy-5,6,7,8-tetrahydro-1-naphthyl)ethenylidene-1,1-diphosphonate 4-Hydroxy-5,6,7,8-tetrahydro-1-naphthaldehyde (0.44 g, 2.5 mmole) and tetra-n-butyl methylene diphosphenate (1.10 g, 2.75 mmole) were treated with titanium tetrachloride and N-methyl morpholine in THF as described in Example 14 to give the title compound as an oil (1.3 g, 92%).

Found: C, 59.49; H, 8.90%. $C_{28}H_{48}O_7P_2$
requires: C, 60.20; H, 8.66%.

EXAMPLE 19

Tetra-n-propyl-2-[4-hydroxy-5,6,7,8-tetra-hydro-1-naphthyl)ethenylidene-1,1-diphosphonate 4-Hydroxy-5,6,7,8-tetrahydro-1-naphthaldehyde (0.44 g, 2.5 mmole) and tetra-n-propyl methylene diphosphonate (0.94 g, 2.75 mmole) were treated with titanium tetracholride and N-methyl morpholine in THF as described in Example 14 to give the title compound as an oil (0.98 g, 78%).

Found: C, 57.00; H, 7.98%. $C_{24}H_{40}O_7P_2$
requires: C, 57.36; H, 8.02%.

EXAMPLE 20

Tetra-i-propyl 2-(4-hydroxy-5,6,7,8-tetrahydro-1-naphthyl)ethenylidene-1,1-diphosphonate 4-Hydroxy-5,6,7,8-tetrahydro-1-naphthaldehyde (0.44 g, 2.5 mmole) and tetra-i-propyl methylene diphosphonate (0.94 g, 2.75 mmole) were treated with titanium tetrachloride and N-methyl morpholine in THF as described in Example 14 to give the title compound as a solid, m.p. 121°–122° (0.247 g, 19.6%).

Found: C, 57.07; H, 7.98% $C_{24}H_{40}O_7P_2$
requires: C, 57.36; H, 8.02%.

EXAMPLE 21

Tetraethyl 2-(4-hydroxy-5,6,7,8-tetrahydro-1-naphthyl)ethenylidene-1,1-diphosphonate 4-Hydroxy-5,6,7,8-tetrahydro-1-naphthaldehyde (0.44 g, 2.5 mmole) and tetraethyl methylene diphosphonate (0.800 g, 2.75 mmole) were treated with titanium tetrachloride and N-methyl morpholine in THF as described in Example 14 to give the title compound as a solid, m.p. 120°–121° (0.89 g, 83%).

Found: C, 53.96; H, 7.18%. $C_{20}H_{32}O_7P_2$
requires: C, 53.81; H, 7.22%

EXAMPLE 22

Tetraethyl 2-(3-tert-butyl-5,5-dimethyl-4-hydroxy-5,6,7,8-tetrahydro-1-naphthyl)ethenylidene-1,1-diphosphonate A solution of titanium chloride (38.0 g, 200 mmole) in dichloromethane was cooled to −50° under argon. To it was added a solution of 2M trimethylaluminium in hexane (100 ml, 200 mmole) under argon. A solution of 8-methoxy-1-tetralone (17.62 g, 100 mmole) in dry dichloromethane (30 ml) was added dropwise at −30°. The mixture was stirred overnight at room temperature, poured slowly onto ice water (1 lit) and extracted with diethyl ether. The organic extract washed with water, aqueous sodium bicarbonate and aqueous saturated sodium chloride, dried and evaporated. The oily residue was chromatographed on silica gel using n-pentane as eluant to give 8,8-dimethyl-1-methoxy-5,6,7,8-tetrahydronaphthalene as a colourless oil (17.23 g, 90.5%).

To a solution of 8,8-dimethyl-1-methoxy-5,6,7,8-tetrahydronaphthalene (16.4 g, 86 mmole) in dry dichloromethane (300 ml), boron tribomide (23.75 g, 91 mmole) was added at −58°. The mixture was stirred and warmed to 0° over 3 hours, poured into ice-water (1 lit) and extracted with diethylether. The ethereal extract was washed with water and aqueous saturated sodium chloride, dried and evaporated. The residue was chromatographed in silica gel using dichloromethane as eluant to give 8,8-dimethyl-5,6,7,8-tetrahydro-1-naphthol as an oil (11.2 g, 73.2%).

To a solution of 8,8-dimethyl-5,6,7,8-tetrahydro-1-naphthol (10.1 g, 57.3 mmole) and tert-butanol (4.25 g, 57.3 mmole) in glacial acetic acid (30 ml) 90% aqueous sulphuric acid (3.0 ml) was added. The mixture was stirred at 40° for 3 hours, poured into water (100 ml) and extracted with diethylether (2×200 ml). The ethereal extract was washed with water and with aqueous saturated sodium chloride, dried and evaporated. The residue was chromatographed on silica gel using a n-pentane: dichloromethane (1:1) mixture to give 2-tert-butyl-8,8-dimethyl-5,6,7,8-tetrahydro-1-naphthol as a colourless oil (9.5 g, 71%).

To a solution of 2-tert-butyl-8,8-dimethyl-5,6,7,8-tetrahydronaphthol (9.5 g, 40.5 mmole) and 1,1-dichloromethyl methyl ether (5.17 g, 45 mmole) in dry dichloromethane (200 ml) stannic chloride (15.63 g, 60 mmole) was added dropwise at −58°. The mixture was warmed to 0° over 45 minutes, poured into ice water (300 ml) and extracted with diethyl ether (3×150 ml). The ether extracts were washed with water and aqueous saturated sodium chloride, dried and evaporated to give 3-tert-butyl-5,5-dimethyl-4-hydroxy-5,6,7,8-tetrahydro-1-naphthaldehyde as a crystalline solid (9.49 g, 90%), m.p. 143°-45°.

3-Tert-butyl-5,5-dimethyl-4-hydroxy-5,6,7,8-tetrahydro-1-naphthaldehyde (1.31 g, 55 mmole) and tetraethyl methylene diphosphonate (158 g, 5.5 mmole) were treated with titanium tetrachloride and N-methyl morpholine in THF as described in Example 14 to give tetraethyl 2-(3-tert-butyl-5,5-dimethyl-4-hydroxy-5,6,7,8-tetrahydronaphthyl)ethenylidene-1,1-diphosphonate as a solid, m.p. 163°-164° (1.63 g, 61%).

Found: C, 59.02; H, 8.39%. $C_{26}H_{44}O_7P_2$
requires: C, 58.86; H, 8.36%

EXAMPLE 23

Tetra-n-propyl 2-(3-tert-butyl-5,5-dimethyl-4-hydroxy-5,6,7,8-tetrahydronaphthyl)ethenylidene-1,1-diphosphonate 3-Tert-butyl-5,5-dimethyl-4-hydroxy-5,6,7,8-tetrahydro-1-naphthaldehyde (2.12 g, 8.15 mmole) and tetra-n-propyl methylene diphosphonate (3.09 g, 9.0 mmole) were treated with titanium tetrachloride and N-methyl morpholine in THF as described in Example 14 to give tetra-n-propyl 2-(3-tert-butyl-5,5-dimethyl-4-hydroxy-5,6,7,8-tetrahydronaphthyl)ethenylidene-1,1-diphosphonate as a solid (2.92 g, 61%), m.p. 125°-26°.

Found: C, 61.59; H, 9.01%. $C_{30}H_{52}O_7P_2$
requires: C, 61.41; H, 8.93%

EXAMPLE 24

Tetra-i-propyl 2-(3-tert-butyl-5,5-dimethyl-4-hydroxy5,6,7,8-tetrahydronaphthyl)ethenylidene-1,1-diphosphonate 3-Tert-butyl-5,5-dimethyl-4-hydroxy-5,6,7,8-tetrahydro-1-naphthaldehyde (1.302 g, 0.005) and tetra-i-propyl methylene diphosphonate (1.89, 5.5 mmole) were treated with titanium tetrachloride and N-methyl morpholine in THF as described in Example 14 to give tetra-i-propyl 2-(3-tert-butyl-5,5-dimethyl-4-hydroxy5,6,7,8-tetrahydronaphthyl)ethenylidene-1,1-diphosphonate as a solid, m.p. 143°-145° (0.4 g, 22.2%).

Found: C, 61.16; 8.91%. $C_{30}H_{52}O_7P_2$
requires: C, 61.41; H, 8.93%.

EXAMPLE 25

Tetra-n-butyl 2-(3-tert-butyl-5,5-dimethyl-4-hydroxy5,6,7,8-tetrahydro-1-naphthyl)ethenylidene-1,1diphosphonate 3-Tert-butyl-5,5-dimethyl-4-hydroxy-5,6,7,8-tetrahydro-1-naphthaldehyde (1.309 g, 5 mmole) and tetra-n-butyl methylene diphosphonate (2.20 g, 5.5 mmole) were treated with titanium tetrachloride and N-methyl morpholine in THF as described in Example 14 to give tetra-n-butyl 2-(3-tert-butyl-5,5-dimethyl-4-hydroxy5,6,7,8-tetrahydro-1-naphthyl)ethenylidene-1,1diphosphonate as a solid, m.p. 97°-98° (1.8 g, 56.0%).

Found: C, 64.08; H, 9.63%. $C_{34}H_{60}O_7P_2$
requires: 63.53; H, 9.41%.

EXAMPLE 26

Tetra-n-propyl 2-6-tert-butyl-7-hydroxy-4-indanyl]ethenylidene-1,1-diphosphonate To a solution of 7-hydroxyindan-1-one (6.0 g, 40 mmole) in trifluoroacetic acid (30 ml), triethylsilane (10.23 g, 87.9 mmole) was added. The mixture was refluxed for 5 hours, poured into water (200 ml) and extracted with diethyl ether (2×200 ml). The extract was washed with water. The ethereal solution was extracted with 4NNaOH (3×50 ml). The alkaline extract was washed with diethyl ether then acidified to pH1 with hydrochloric acid. The aqueous mixture was extracted with diethyl ether and the ethereal extract was washed with water and aqueous saturated sodium chloride, was dried, and the solvents evaporated to give 4-hydroxyindane as a colourless oil (4.9 g, 90%).

To 4-hydroxyindane (4.9 g, 36 mmole) and tert-butanol (2.67 g, 36 mmole) in glacial acetic acid (10 ml), 90% sulphuric acid (1 ml) was added and the mixture stirred at 40° for two hours followed by further addition of tert-butanol (1.79 g, 24 mmole) and stirring for an additional hour at 40°. The mixture was poured into water and extracted with diethyl ether (2×100 ml). The ethereal extract was washed with water and aqueous saturated sodium chloride and dried. Having evaporated off the solvents the residue was chromatographed on silica gel using dichloromethane to give an oil (6.82 g) which was treated with 1,1-dichloro methyl methyl ether (4.6 g, 40 mmole) and stannic chloride (13.0 g, 50 mmole) at −40°. The mixture was allowed to stand at 5° for 16 hours, poured into ice-water (200 ml) and extracted with ethyl acetate. The organic extract was washed with water and aqueous saturated sodium chloride and dried. The solvents were evaporated off and the residue triturated with diethyl ether and pentane to give 6-tert-butyl-7-hydroxyindan-4-carboxaldehyde as a colourless crystalline solid, m.p. 213°-214° (1.95 g, 22%).

To dry tetrahydrofuran (30 ml) was added titanium tetrachloride (1.73 g, 10 mmole) at −58° followed by 6-tert-butyl-7-hydroxyindane-4-carboxaldehyde (0.88 g, 4 mmole) and tetra-n-propyl methylene diphosphonate (1.52 g, 4.41 mmole). N-Methyl-morpholine (2.05 g, 20 mole) was added dropwise at −10° to +5°. The mixture was stirred for 3.25 hours at room temperature. It was poured into ice-water (100 ml) and extracted with diethyl ether (2×150 ml). The extract was washed with water and aqueous saturated sodium chloride and dried. The residue obtained on evaporating the solvent was chromatographed on silica gel using ethyl acetate as eluant. After trituration with diethyl ether:n-pentane mixture, the title compound was obtained as a colourless crystalline solid (1.03 g, 47.2%), m.p. 109°-110°.

Found: C, 59.54%; H, 8.56%. $C_{27}H_{46}O_7P_2$ requires C, 59.55%; H, 8.51%.

EXAMPLE 27

Tetra-n-butyl 2-[6-tert-butyl-7-hydroxy-4-indanyl]ethenylidene-1,1-diphosphonate Titanium tetrachloride (1.73 g, 10 mmole) was added to dry tetrahydrofuran (30 ml) at −58°. 6-Tert-butyl-7-hydroxyindan-4-carboxaldehyde (0.88 g, 4 mmole) and tetra-n-butyl methylene diphosphonate (1.76 g, 4.4 mmole) were added to the mixture. N-methyl morpholine (2.05 g, 20 mmole) was added dropwise between −10° to 5°. The mixture was stirred for 3.25 hours at room temperature and poured into ice water (100 ml), and extracted with diethyl ether (3×100 ml). The extract was washed with water and aqueous saturated sodium chloride and dried. The residue obtained on evaporating the solvent was chromatographed on silica gel using ethyl acetate as elutant to give the title compound as a crystalline solid on trituration with n-pentane and diethyl ether (1 36 g, 56.6%), m p 65°-66°.

Found: C, 62.29%; H, 9.14%. $C_{31}H_{54}O_7P_2$ requires: C, 61.98%; H, 9.06%

EXAMPLE 28

Tetra-n-butyl-2-(4-hydroxy-3-methyl)-ethylidiene-1,1diphosphonate

To a stirred solution of titanium tetrachloride (2.10 g, 11 mole) in dry tetrahydrofuran (30 ml) at −58 degrees C., 4-hydroxy-3-methyl-1-naphthaldehyde (0.94 g, 5 mole) and tetra-n-butyl methylene diphosphonate (2.20 g, 5.5 mole) were added, and the reaction mixture warmed to −10 degrees C. N-methyl morpholine (2.45 g, 24.2 mole) was added dropwise such that the reaction temperature did not exceed 10 degrees C. The reaction mixture was stirred for 3.24 hours at room temperature and was then poured on to ice-water (100 ml). It was extracted with diethyl ether (3×100 ml) and the ethereal extract was washed with water and then aqueous saturated sodium chloride, dried and evaporated and the residue chromatographed on silica gel using ethyl acetate as eluant to give tetra-n-butyl 2-(4-hydroxy-3-methyl)-ethylidiene-1,1-diphosphonate as a yellow oil (2.58 g, 91%)

Found: C, 60.54%, H, 8.39%, C29 H46 07 P2 0.4H2O requires C, 60.48%, H, 8.19%.

EXAMPLE A

| Capsule Formulation: | mg/Capsule |
|---|---|
| Compound of Structure (I) | 300 |
| Gelatin | 100 |
| Polyethylene Glycol 1000 | 600 |
| Potassium Sorbate | 0.5 |

EXAMPLE B

| Tablet Formulation: | mg/Tablet |
|---|---|
| Compound of Structure (I) | 500 |
| Hydroxy Propyl Methyl Cellulose | 500 |
| Magnesium Stearate | 3 |

Biological Data

A. Inhibition of Acyl-CoA:Cholesterol Acyltransferase (ACAT) in rat liver microsomes The compounds were assayed for ACAT activity in freeze-dried cholesterol-fed rat liver microsomes. Each assay comprised 0.4 mg of protein with BSA (0.5 mg), glutathione (0.5 mg), and sufficient buffer (0.05M K2HPO4 +0.05M NaF, pH 7.4) to bring the volume to 500 ml. Inhibitors were dissolved in DMSO at such a concentration that they could be added in 10 ml, and added to the above. After a 15 minutes preincubation, the reaction was started by adding 38.8 nmoles of oleoyl CoA with approximately 30000 dpm of [14C]oleoyl CoA.

The assays were incubated at 37° for 3 minutes and the reaction terminated by adding methanol (1 ml). To allow correction for the recovery of products, approximately 25000 dpm of [3H]cholesteryl oleate was added. Lipids were extracted into chloroform:methanol (2:1), evaporated to dryness, redissolved in petroleum spirit and the labelled cholesteryl oleate separated from the labelled substrate on a silica bond-elute column. The amount of product formed was determined by liquid scintillation counting.

The compounds of Examples 1 to 6, 8, 10 to 12, 14 to 16, 18 to 20, 23, 26 and 27 were found to have $IC_{50}$ values in the range of from 1.3 to 50 μM.

B. Antioxidant Activity

Rat liver homogenates were prepared according to Fraga, C. G. et al. Free Radicals Biol. Med., 4, 155, 1988 and Kornburst D. J. et al. Lipids 15, 315, 1980.

Peroxides were generated by incubation of the homogenate with the FeSO4 as described by Quitanilha A. T. et al. Ann. N.Y., Acad. Sci. 393, 32, 1982.

Compounds to be tested for their antioxidant activity were dissolved in DMSO and added to the incubation mixture. The amount of peroxide produced was determined by the thiobarbituric acid reaction using malonaldehyde as standard.

In this screen, the compounds of examples 1, 2, 6 and 8 had $IC_{50}$ values (μM) of 1.5, 0.7, 7.0 and 2.5 respectively.

We claim:

1. A compound of structure (I) :

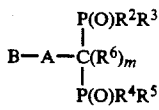

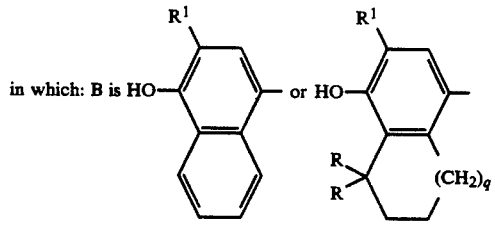

where
R is hydrogen or $C_{1-4}$alkyl and q is 0 or 1;
$R^1$ is hydrogen or $C_{1-8}$alkyl;
$R^2$, $R^3$, $R^4$ and $R^5$ are the same or different and are $OR^7$ in which $R^7$ is hydrogen or $C_{1-8}$alkyl; or $R^2$ and $R^3$ together and $R^4$ and $R^5$ together form a $C_{2-8}$alkylene dioxy ring;
$R^6$ is hydrogen or $C_{1-4}$alkyl;
m is 0 or 1, and
A is S, $S(CH_2)_n$, $CH=CHCH_2$, $(CH_2)_n$ or $(CH=CH)_p(CH_2)_tCH=$ in which n is 1 to 7, p is 0 or 1 and t is 0 to 4, with the proviso that m is 0 only when A is $(CH=CH)_p(CH_2)_tCH=$.

2. A compound of structure (I) as claimed in claim in which $R^1$ is $C_{1-8}$alkyl.

3. A compound of structure (I) as claimed in claim 2 in which $R^2$, $R^3$, $R^4$ and $R^5$ are all the same and are $OR^7$ in which $R^7$ is $C_{1-8}$alkyl.

4. A compound of structure (I) as claimed in claim 3, in which A is $(CH=CH)_p(CH_2)_tCH=$ and p and t are both zero.

5. A compound of structure (I) as claimed in claim

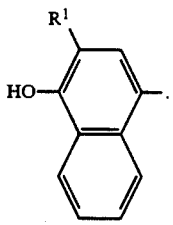

6. A compound of structure (I) as claimed in claim

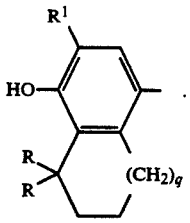

7. A compound of structure (I) as claimed in claim 1 which is:
tetraethyl-2-[3-t-butyl-4-hydroxy-1-naphthyl]ethenylidene-1,1-diphosphonate.

8. A compound of structure (I) as claimed in claim 1 which is:
tetraisopropyl 2-[3-t-butyl-4-hydroxy-1-naphthyl]ethenylidene-1,1-diphosphonate.

9. A compound of structure (II as claimed in claim 1 which is:
tetraethyl-2-(3-tert-butyl-4-hydroxy-5,6,7,8-tetrahydro-1-naphthyl)-ethenylidene-1,1-diphosphonate.

10. A compound of structure (I) as claimed in claim 1 which is:
tetraisopropyl-2-[3-tert-butyl-4-hydroxy-5,6,7,8-tetrahydro1-naphthyl]-ethenylidene-1,1-diphosphonate.

11. A compound of structure (I) as claimed in claim 1 which is:
tetra-n-propyl 2-[3-tert-butyl-4-hydroxy-1-naphthyl]ethenylidene-1,1-diphosphonate.

12. A compound of structure (I) as claimed in claim 1 which is:
tetra-n-propyl 2-[3-tert-butyl-4-hydroxy-5,6,7,8tetrahydro-1-naphthyl]ethenylidene-1,1-diphosphonate.

13. A compound of structure (I) as claimed in claim 1 which is:
tetraethyl 2-(3-tert-butyl-5,5-dimethyl-4-hydroxy-5,6,7,8-tetrahydro-1-naphthyl)ethenylidene-1,1-diphosphonate.

14. A compound of structure (I) as claimed in claim 1 which is:
tetra-n-propyl 2-(3-tert-butyl-5,5-dimethyl-4-hydroxy-5,6, 7,8-tetrahydro-1-naphthyl)ethenylidene-1-diphosphonate.

15. A compound of structure (I) as claimed in claim 1 which is:
tetra-i-propyl 2-(3-tert-butyl-5,5-dimethyl-4-hydroxy-5,6, 7,8-tetrahydro-1-naphthyl)ethenylidene-1-diphosphonate.

16. A compound of structure (I) as claimed in claim 1 which is:
tetra-n-propyl 2-[6-tert-butyl-7-hydroxy-4-indanyl]ethenylidene-1,1-diphosphonate.

17. A pharmaceutical composition comprising a compound of structure (I) as claimed in claim 1 in association with a pharmaceutically acceptable carrier.

18. A method of treatment of hyperlipidaemia which comprises administering to a mammal in need thereof an effective amount of a compound according to claim 1.

19. A method of inhibiting the enzyme acyl-CoA:-cholesterolacyltransferase which comprises administering to a subject in need thereof an effective amount of a compound according to claim 1.

20. A compound of structure (I) as claimed in claim 1 which is:
tetra-n-propyl 2-[4-hydroxy-3-methyl-1-naphthyl]ethenylidene-1,1-diphosphonate.

21. A compound of structure (I) as claimed in claim 1 which is:
tetra-n-butyl 2-(3-tert-butyl-5,5-dimethyl-4-hydroxy-5,6,7,8-tetrahydro-1-naphthyl)ethenylidene-1,1diphosphonate.

22. A compound of structure (I) as claimed in claim 1 which is:
tetra-n-butyl 2-4-hydroxy-3-methyl)-ethenylidene-1,1-diphosphonate.

23. A composition of claim 17 wherein the compound is:
tetra-n-propyl 2-[3-tert-butyl-4-hydroxy-1naphthyl]-ethenylidene-1,1-diphosphonate.

24. A composition of claim 17 wherein the compound is tetra-n-propyl 2-[4-hydroxy-3-methyl-1-naphthyl]-ethenylidene-1,1-diphosphonate.

25. A composition of claim 17 wherein the compound is:
tetraethyl 2-(3-tert-butyl-5,5-dimethyl-4-hydroxy-5,6,7,8-tetrahydro-1-naphthyl)ethenylidene-1,1-diphosphonate.

26. A composition of claim 17 wherein the compound is:
tetra-n-propyl 2-(3-tert-butyl-5,5-dimethyl-4-hydroxy-5,6,7,8-tetrahydro-1-naphthyl)ethenylidene-1,1-diphosphonate.

27. A composition of claim 17 wherein the compound is:
tetra-i-propyl 2-(3-tert-b,utyl-5,5-dimethyl-4-hydroxy-5,6,7,8-tetrahydro-1-naphthyl)ethenylidene-1,1-diphosphonate.

28. A composition of claim 17 wherein the compound is:
tetra-n-butyl 2-(3-tert-butyl-5,5-dimethyl-4-hydroxy-5,6,7,8-tetrahydro-1-naphthyl)ethenylidene-1,1-diphosphonate.

29. A composition of claim 17 wherein the compound is:
tetra-n-butyl 2-(4-hydroxy-3-methyl)-ethenylidene-1,1-diphosphonate.

30. A method of claim 18 wherein the compound is tetra-n-propyl 2-[3-tert-butyl-4-hydroxy-1-naphthyl-]ethenylidene-1,1-diphosphonate.

31. A method of claim 18 wherein the compound is tetra-n-propyl 2-[4-hydroxy-3-methyl-1-naphthyl]ethenylidene-1,1-diphosphonate.

32. A method of claim 18 wherein the compound is tetraethyl 2-(3-tert-butyl-5,5-dimethyl-4-hydroxy-5,6,7,8-tetrahydro-1-naphthyl)ethenylidene-1,1diphosphonate.

33. A method of claim 18 wherein the compound is tetra-n-propyl 2-(3-tert-butyl-5,5-dimethyl-4-hydroxy-5,6,7,8-tetrahydro- 1-naphthyl)ethenylidene-1,1-diphosphonate.

34. A method of claim 18 wherein the compound is tetra-i-propyl 2-(3-tert-butyl-5,5-dimethyl-4-hydroxy-5,6,7,8-tetrahydro-1-naphthyl)ethenylidene-1,1-diphosphonate.

35. A method of claim 18 wherein the compound is tetra-n-butyl 2-(3-tert-butyl-5,5-dimethyl-4-hydroxy-5,6,7,8-tetrahydro-1-naphthyl)ethenylidene-1,1-diphosphonate.

36. A method of claim 18 wherein the compound is tetra-n-butyl 2-(4-hydroxy-3-methyl)-ethylidene-1,1-diphosphonate.

37. A method of claim 19 wherein the compound is tetra-n-propyl 2-[3-tert-butyl-4-hydroxy-1-naphthyl-]ethenylidene-1,1-diphosphonate.

38. A method of claim 19 wherein the compound is tetra-n-propyl 2-[4-hydroxy-3-methyl-1-naphthyl]ethenylidene-1,1-diphosphonate.

39. A method of claim 19 wherein the compound is tetraethyl 2-(3-tert-butyl-5,5-dimethyl-4-hydroxy-5,6,7,8-tetrahydro-1-naphthyl)ethenylidene-1,1-diphosphonate.

40. A method of claim 19 wherein the compound is tetra-n-propyl 2-(3-tert-butyl-5,5-dimethyl-4-hydroxy-5,6,7,8-tetrahydronaphthyl)ethenylidene-1,1-diphosphonate.

41. A method of claim 19 wherein the compound is tetra-i-propyl 2-(3-tert-butyl-5,5-dimethyl-4-hydroxy-5,6,7,8-tetrahydronaphthyl)ethenylidene-1,1-diphosphonate.

42. A method of claim 19 wherein the compound is tetra-n-butyl 2-(3-tert-butyl-5,5-dimethyl-4-hydroxy-5,6,7,8-tetrahydro-1-naphthyl)ethenylidene-1,1-diphosphonate.

43. A method of claim herein the compound is tetra-n-butyl 2-(4-hydroxy-3-methyl-ethylidene-1,1-diphosphonate.

* * * * *